United States Patent
Damaser et al.

(10) Patent No.: US 10,143,391 B2
(45) Date of Patent: Dec. 4, 2018

(54) IMPLANTABLE PRESSURE SENSOR

(71) Applicant: CASE WESTERN RESERVE UNIVERSITY, Cleveland, OH (US)

(72) Inventors: Margot S. Damaser, Cleveland Heights, OH (US); Steven Majerus, Cleveland, OH (US); Paul C. Fletter, Mt. Prospect, IL (US); Steven L. Garverick, Cleveland Hts., OH (US); Wen H. Ko, Cleveland Hts., OH (US); Paul Zaszczurynski, Sycamore, IL (US)

(73) Assignees: CASE WESTERN RESERVE UNIVERSITY, Cleveland, OH (US); THE CLEVELAND CLINIC FOUNDATION, Cleveland, OH (US); THE UNITED STATES OF AMERICA AS REPRESENTED BY THE DEPARTMENT OF VETERNS AFFAIRS, Washington, DC (US)

( * ) Notice: Subject to any disclaimer, the term of this patent is extended or adjusted under 35 U.S.C. 154(b) by 51 days.

(21) Appl. No.: 13/889,852

(22) Filed: May 8, 2013

(65) Prior Publication Data
US 2013/0303942 A1 Nov. 14, 2013

Related U.S. Application Data

(60) Provisional application No. 61/643,988, filed on May 8, 2012.

(51) Int. Cl.
*A61B 5/03* (2006.01)
*A61B 5/00* (2006.01)
*A61B 5/20* (2006.01)

(52) U.S. Cl.
CPC ............ *A61B 5/03* (2013.01); *A61B 5/205* (2013.01); *A61B 5/6874* (2013.01);
(Continued)

(58) Field of Classification Search
CPC ................................. A61B 5/03; A61B 5/00
See application file for complete search history.

(56) References Cited

U.S. PATENT DOCUMENTS 7,668,596 B2   2/2010 Von Arx et al.
2002/0161304 A1 * 10/2002 Eide ............................ 600/485
(Continued)

FOREIGN PATENT DOCUMENTS

WO          9106336 A1    5/1991

OTHER PUBLICATIONS

Bannowsky et al., "Dependence on the Type of Anesthesia to Induce Bladder Instabilities in an Animal Model", The Journal of Urology, 2011, vol. 185, No. 4S, p. e317.
(Continued)

*Primary Examiner* — Daniel Cerioni
*Assistant Examiner* — Yasmeen S Warsi
(74) *Attorney, Agent, or Firm* — Tarolli, Sundheim, Covell & Tummino LLP

(57) ABSTRACT

Systems and methods are provided for in vivo measurement of pressure. An implantable sensor assembly includes a pressure sensor configured to provide an analog signal representing pressure and a signal conditioning component configured to convert the pressure sensor output into a digital signal. A transmitter is configured to transmit the digital signal to an external base unit. A power control unit is configured to dynamically allocate power throughout the implantable sensor assembly, such that during an active measurement interval of the implantable sensor assembly, each of the pressure sensor, the signal conditioning compo-
(Continued)

nent, and the transmitter are powered only for a portion of the active measurement interval necessary to perform a related function.

9 Claims, 3 Drawing Sheets

(52) U.S. Cl.
    CPC .......... *A61B 5/6882* (2013.01); *A61B 5/726* (2013.01); *A61B 2560/0219* (2013.01)

(56) References Cited

U.S. PATENT DOCUMENTS

2003/0100839 A1  5/2003  Cohen et al.
2007/0156205 A1  7/2007  Larson et al.

OTHER PUBLICATIONS

Belloni et al., "Low-Power Ripple-Free Chopper Amplifier with Correlated Double Sampling De-Chopping", pp. 765-768.

Enz et al., "Circuit Techniques for Reducing the Effects of Op-Amp Imperfections: Autozeroing, Correlated Double Sampling, and Chopper Stabilization", Proceedings of the IEEE, 1996, vol. 84, No. 11, pp. 1584-1614.

Fletter et al., "Wireless Micromanometer System for Chronic Bladder Pressure Monitoring", pp. 1-3.

Kurstjens "Sacral Root Afferent Nerve Signals for a Bladder Neuroprosthesis: From Animal Model to Human", Ph. D. Thesis, 2008, pp. 1-112.

Majerus, et al. "Low-Power Wireless Micromanometer System for Acute and Chronic Bladder-Pressure Monitoring", IEEE Transactions on Biomedical Engineering, 2011, vol. 58, No. 3, pp. 763-767.

Majerus et al., "Wireless, Ultra-Low-Power Implantable Sensor for Chronic Bladder Pressure Monitoring", ACM Journal on Emerging Technologies in Computing Systems, 2012, vol. 8, No. 2, Article 11, pp. 1-13.

Valdastri et al., "An Implantable ZigBee Ready Telemetric Platform for In Vivo Monitoring of Physiological Parameters", Sensors and Actuators, 2008, A 142, pp. 369-378.

Wang et al., "A Mini-Invasive Long-Term Bladder Urine Pressure Measurement ASIC and System", IEEE Transactions on Biomedical Circuits and Systems, 2008, vol. 2, No. 1, pp. 44-49.

Yoshida et al., "A 1 V Low-Noise CMOS Amplifier Using Autozeroing and Chopper Stabilization Technique", IEICE Trans. Electron., 2006, vol. E89-C, No. 6, pp. 769-774.

PCT International Search Report and Written Opinion for PCT/US2013/040125, dated Dec. 10, 2013, pp. 1-21.

European Office Action corresponding to European Patent Application No. 13724109.7, dated Aug. 18, 2017, pp. 1-8.

* cited by examiner

10,143,391 B2

IMPLANTABLE PRESSURE SENSOR

RELATED APPLICATION

This application claims priority from U.S. Provisional Patent Application Ser. No. 61/643,988, filed 8 May 2012, the subject matter of which is incorporated hereby incorporated by reference in its entirety.

FIELD OF THE INVENTION

The present invention relates to systems and methodologies for diagnosis of medical conditions, and, in particular, is directed to systems and methods in vivo pressure measurement.

BACKGROUND OF THE INVENTION

Physiological pressure measurements are useful for medical diagnosis and monitoring in many medical disciplines, such as cardiology, pulmonology, gastroenterology, and urology. Blood pressure is one of the few physiological pressures that can be measured noninvasively with a sphygmomanometer, but other pressures are typically measured via catheters, either connected to transducers outside the body or by micro-transducers mounted on the tip.

SUMMARY OF THE INVENTION

In accordance with an aspect of the present invention, an implantable sensor assembly includes a pressure sensor configured to provide an analog signal representing pressure and a signal conditioning component configured to convert the pressure sensor output into a digital signal. A transmitter is configured to transmit the digital signal to an external base unit. A power control unit is configured to dynamically allocate power throughout the implantable sensor assembly, such that during an active measurement interval of the implantable sensor assembly, each of the pressure sensor, the signal conditioning component, and the transmitter are powered only for a portion of the active measurement interval necessary to perform a related function.

In accordance with another aspect of the present invention, a pressure monitoring system includes an implanted pressure sensor assembly and an external base unit. The implanted pressure sensor assembly includes a pressure sensor configured to provide an analog signal representing pressure and a signal conditioning component configured to convert the pressure sensor output into a digital signal. A transmitter is configured to transmit the digital signal to an external base unit. The implanted pressure assembly further includes a microbattery, a power control unit configured to dynamically allocate power from the microbattery throughout the implantable sensor assembly, and a recharge component configured to inductively charge the microbattery in the presence of the transmitted radio frequency (RF) energy. The external base unit includes a receiver configured to receive the digital signal from the transmitter and a recharger configured to transmit RF energy to the recharge component, with a transmitted power of the recharger being responsive to the digital signal.

In accordance with yet another aspect of the present invention, a method is provided for determining a pressure from an in vivo sensor. A digital signal is received from the in vivo sensor. A windowing function is applied to the digital signal to isolate a portion of the digital signal representing a series of pressure measurements. A multi-resolution wavelet analysis is applied to the isolated portion of the digital signal to provide a transformed signal. Classification features are extracted from the transformed signal, and the signal is classified into one of a plurality of event classes according to the extracted classification features.

BRIEF DESCRIPTION OF THE DRAWINGS

The foregoing and other features of the present invention will become apparent to those skilled in the art to which the present invention relates upon reading the following description with reference to the accompanying drawings, in which.

DETAILED DESCRIPTION OF THE INVENTION

Figure 1:
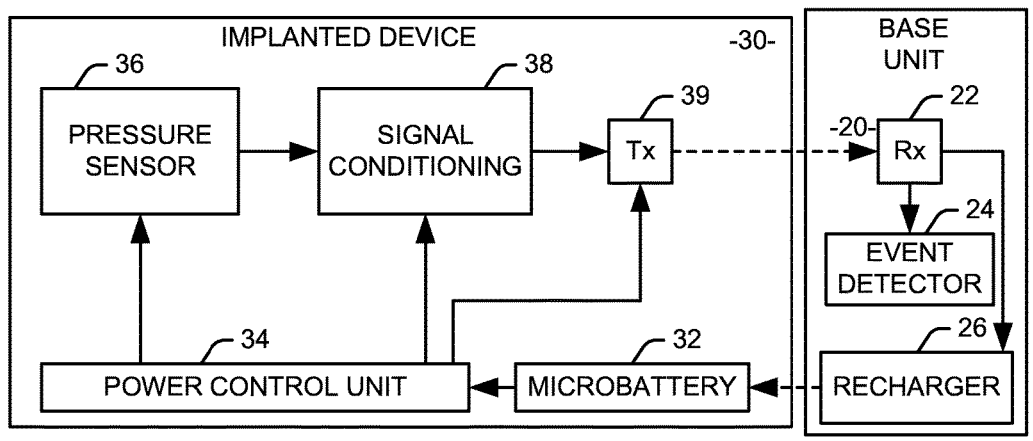
FIG. 1 illustrates a pressure sensing system in accordance with an aspect of the present invention.

FIG. 1 illustrates a pressure sensing system 10 in accordance with an aspect of the present invention. The system 10 comprises an external base unit 20, comprising a radio frequency (RF) receiver 22, a signal processor 24, and a recharger 26 for transmitting RF energy, and an implanted device 30. The RF receiver 22 is configured to receive data communicated from the implanted device, and is specifically configured to capture very short transmission pulses from the implanted device. It will be appreciated that the external base unit 20 can include further devices (e.g., for detecting pressure in the ambient environment) that are not shown in FIG. 1.

The signal processor 24 evaluates the received pressure data to extract useful information from electrical and biological noise. The recharger 26 uses a Class-E amplifier and a tuned transmitting coil to inductively transmit RF energy to the implanted device 30. In one implementation, the recharger 26 uses less than ten watts of external RF power to provide, at a maximum separation of twenty centimeters, seven hundred microwatts of power to the implanted device 30. The base unit 20 uses inductive antennas to receive pressure telemetry from the implanted device 30 and to send power and commands to an implanted battery 32 and a power control unit 34, respectively. In one implementation, the receiver 22 is portable and battery powered, but wireless recharging through the recharger 26 utilizes alternating current (AC) line power.

The implanted device 30 can include devices for implementation with body tissue, such as organ walls, or within fluid filled cavities, such as the bladder, vertebral discs, or the subsrachnoid space. The implanted device 30 includes a pressure sensor 36 configured to determine a pressure in the region in which the device is implanted. In one implementation, the pressure sensor 36 is implemented as a microelectromechanical systems (MEMS) transducer. A signal conditioning component 38 amplifies the output of the pressure sensor 36 and converts the pressure sensor output into a digital signal. An RF transmitter 39 packetizes the digital signal and transmits it to the RF receiver 22. In one implementation, each of the signal conditioning component 38, the RF transmitter 39, and the power control unit 34 are implemented on a single application-specific integrated circuit (ASIC) chip.

In accordance with an aspect of the present invention, the power control unit 34 can dynamically allocate power throughout the implanted device. Unlike standard low-duty-cycle sampling methods, the power control unit 34 does not simply gate power to the instrumentation and telemetry system, but instead operates as a "sample conveyer", in which various functions are provided with power only at points in an acquire/process/transmit cycle when they are needed to acquire, process, or transmit the data sample. It will be appreciated that this differs from a standard sleep mode, as various components are selectively deprived of power even during the active time of the device. Use of the "sample conveyer" technique greatly reduces the power consumption of the system, since circuits like the pressure sensor 36 and an analog-to-digital converter and front-end amplifier associated with the signal conditioning component 38 can be disabled after the sampled information has been passed to a next processing stage. The power usage of the system is dynamic, but the time-averaged current draw is far less than the peak.

It will be appreciated that receiving and processing a wireless signal from a low-power, in vivo device is not trivial even when the device is continuously transmitting in full-power mode. The pulse transmissions that are transmitted intermittently from an implanted device 30 in accordance with an aspect of the present invention provide an additional challenge. Accordingly, the receiver 22 has been designed to use a quadrature detector instead of a phase-locked loop as well as an intermediate frequency limiting amplifier with very fast signal strength detection. The receiver 22 can therefore lock onto a carrier tone in a few microseconds. Demodulation and decoding of the received signal is performed by a complex programmable logic device that checks for edges and glitches and uses majority vote algorithms for clock and data recovery. A microcontroller provides an interface to the event detector 24. In one implementation, the event detector 24 is implemented as machine executable instructions stored on a non-transitory computer readable medium and executed by an associated processor. For example, software running on a general purpose computer can be used to detect events as well as to store and display received signals.

In accordance with another aspect of the present invention, to improve the power-transfer efficiency, the sensing system 10 incorporates power status feedback. The recharge rate of the system 10 is determined by the amount of received energy. If the received energy is too large, the circuitry must dissipate the excess in the form of heat to avoid damage to the battery. Power status feedback would enable the external recharger 26 to continuously know how much RF energy is actually making it to the implantable device, such that it would not transmit more energy than is needed. To this end, the power control unit 34 can determine if sufficient energy is being received to allow for a successful battery recharge and convey this information to the signal conditioning component 38. A single bit is provided into outgoing telemetry packets from the transmitter 39 to indicate whether the implant is receiving enough external RF power for successful battery recharge. If the received power is too low, the power status bit would be 0, indicating that the external RF recharger 26 should increase its transmitted power. If the power status bit remains at 1 for a predetermined length of time, the transmitted power can be gradually lowered until a 0 is received. This system functions automatically to maximize the efficiency of the wireless recharge method while minimizing patient exposure to strong electromagnetic fields.

In one implementation, the implanted device 30 is intended for long-term monitoring pressure within a bladder, either for diagnostic purposes or for providing feedback for various treatments, such as electrical stimulation, radiation, or pharmacology. For example, the system 10 can provide bladder pressure feedback for electrical stimulation bladder control systems as part of treatment for voiding dysfunction or urinary incontinence. This is particularly advantageous for spinal cord injured patients and other patient populations, such as those with multiple sclerosis, who have neurogenic bladder complications of neurological conditions. It is important for chronic bladder monitoring that the device not become a nidus for urinary stones, so in such implementations the implanted device can be being implanted submucosally into the wall of the bladder where it can monitor bladder pressures continuously and over the long term. In such a case, the implanted device 30 can include thin packaging and a flat broad shape.

In another implementation, the system 10 can be used during short-term monitoring of the bladder. The implanted device 30 would be inserted during an office visit, and the patient would go home with it and participate in activities of daily living that cause the incontinence and/or voiding dysfunction. The device would record data or transmit the data to a recorder worn outside the body continuously or when initiated by patient activation. The patient would then return to the doctor's office in a few days or a week to have the device extracted and the data read. It is likely that any submucosal implant will irritate the bladder for a few days or a week after implantation. Therefore a short-term implant whose purpose is diagnostic should not be implanted submucosally as it will change the state of the bladder it is intended to measure and diagnose. Since it is in the bladder for such a short duration, it is not likely to become a nidus for stones in that time.

In a short-duration diagnostic implementation of the system, the implanted device is configured to float in the bladder so as to not become a plug during voiding. One embodiment of the short-duration device would not have a battery on the device itself but would be powered by an external device that would also record the data. The housing for the electronics in the short-duration device would be designed to increase buoyancy of the device. The device itself could be inflated with a lighter than water substance after insertion through the urethra, or it could be constructed of a material that would expand after insertion through the urethra. One embodiment of the short-duration pressure monitoring device would include measurement of bladder volume, which may assist in diagnosis of type of incontinence and/or voiding dysfunction and could better guide treatment.

Both the chronic and the short-duration devices are envisioned to be implanted using a cystoscope, standard in urology clinics and hospitals. The short-duration device would be extracted also using a cystoscope. The material used to inflate the balloon could be extracted and the device extracted once reduced in size. Alternatively, material that expanded after insertion could be contracted once again, and the device would be extracted through the urethra using the cystoscope. An alternate embodiment would utilize an application-specific insertion and extraction device which could be developed to meet the specific needs of either the chronic or short-duration device.

Figure 2:
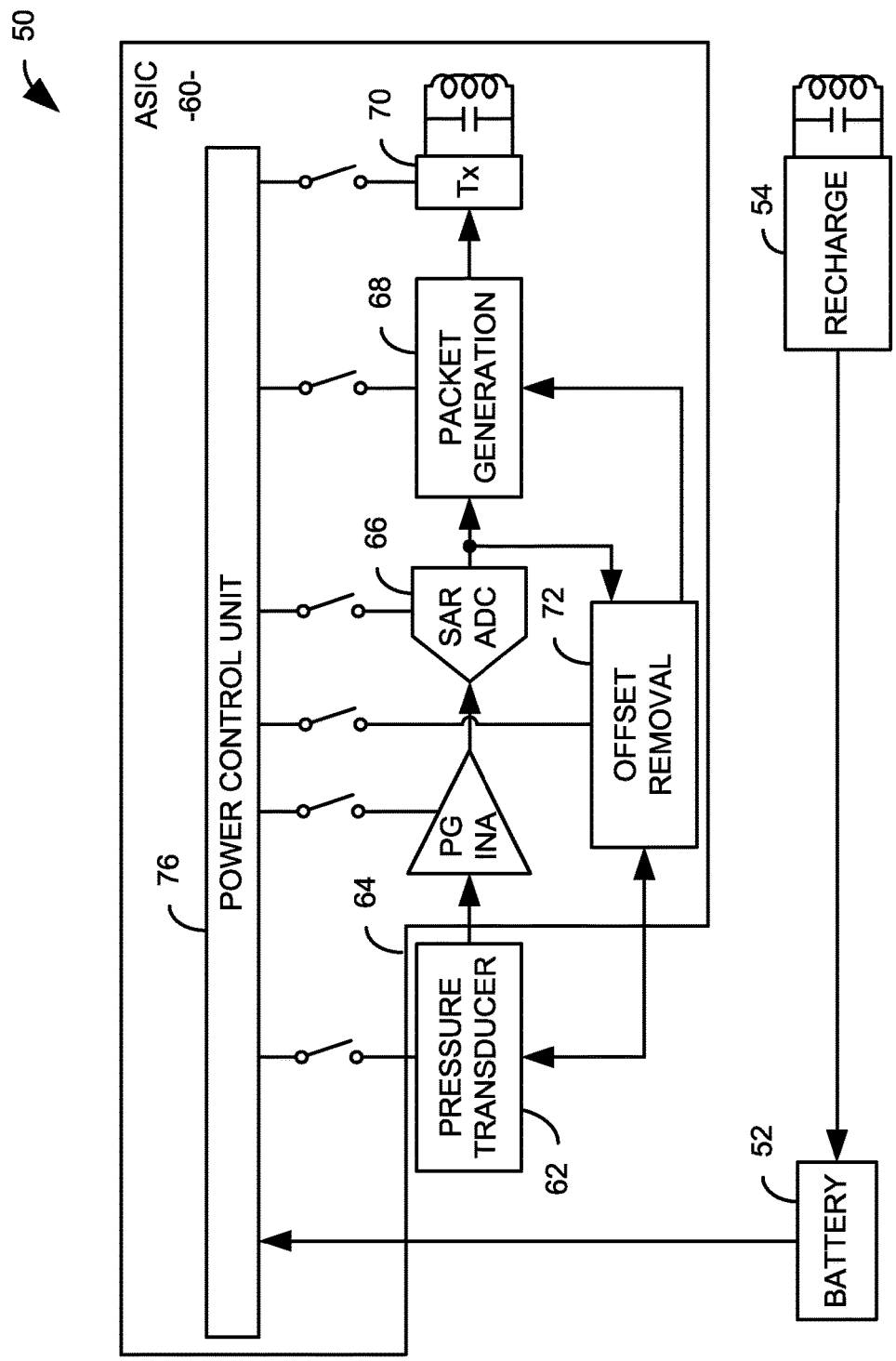
FIG. 2 illustrates one implementation of a sensor assembly in accordance with an aspect of the present invention.

FIG. 2 illustrates one implementation of a sensor assembly 50 in accordance with an aspect of the present invention. In the illustrated implementation, the sensor assembly 50 is intended for submucosal implantation within a human bladder, although it will be appreciated that systems in accordance with the present invention can be suitable for use in other organs, as well as in non-humans or other closed systems. The illustrated sensor assembly 50 includes a microbattery 52 and associated circuitry so that it can be recharged wirelessly and wirelessly transmit continuous pressure telemetry. The sensor 50 is sized so it can be inserted into a human bladder via the urethra and implanted into a submucosal location with either a cystoscope or an application specific insertion tool. After healing, the mucosal layer is strong enough to securely retain the sensor assembly 50, and lumen pressure can be accurately measured through the urothelium. The applications for pressure monitors are multiple and include diagnosis as well as monitoring and feedback to various treatments, such as electrical stimulation, radiation, or pharmacology. In one implementation, the sensor assembly 50 can provide bladder pressure feedback for electrical stimulation bladder control systems.

Electrical stimulation of nerves can arrest unwanted reflex bladder contractions in spinal cord injury patients. Open-loop continuous electrical stimulation can inhibit overactive bladder activity and several devices are approved by the FDA. However, patients must frequently return to the doctor to have their stimulation system adjusted when its effectiveness wanes due to habituation or accommodation to an electrical stimulation signal that is always on. Conditional or closed-loop stimulation that only stimulates when triggered to do so is more effective than open-loop continuous stimulation, resulting in greater bladder capacity and utilizing less power. However, conditional stimulation is presently only utilized acutely for research purposes using catheter-based pressure-sensing systems since a chronic bladder sensor is not available. The illustrated sensor assembly 50 represents a miniature, wireless, catheter-free, battery-powered, rechargeable pressure monitor for chronic submucosal implantation which could provide feedback for chronic conditional stimulation.

To this end, the proposed sensor assembly 50 runs primarily from the microbattery 52 and is charged inductively via a recharge component 54 during six-hour periods, for example, when the user is sleeping. In the illustrated implementation, the battery 52 and associated recharger 54 consume more than half of the volume of the sensor assembly 50, as the active circuitry of the system is implemented on a custom application-specific integrated circuit (ASIC) 60. It will be appreciated that the recharge component 54 can include some signal processing capabilities to receive a set of prespecified commands from the base unit.

A pressure transducer 62 provides an electrical signal representative of an ambient pressure of the environment in which the sensor assembly 50 is implanted. In one example, the pressure transducer 62 can be implemented as a piezoresistive transducer, although it will be appreciated that other implementations can be used within the spirit of the present invention. The signal from the pressure transducer 62 is provided to a programmable gain (PG) instrumentation amplifier (INA) assembly 64 to amplify the transducer output signal before analog-to-digital conversion.

Figure 3:
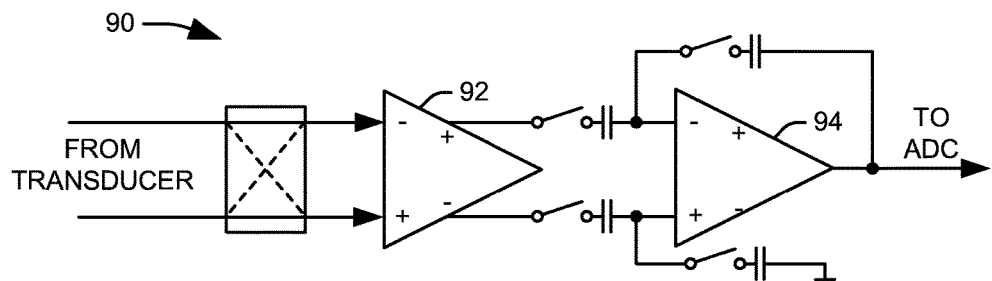
FIG. 3 illustrates an exemplary amplifier assembly in accordance with an aspect of the present invention.

In accordance with an aspect of the present invention, the amplifier architecture provides a low input-referred noise and a small die layout area while maintaining a high input impedance. FIG. 3 illustrates an exemplary amplifier assembly 90 in accordance with an aspect of the present invention. The amplifier assembly 90 includes a chopper-stabilized, continuous time, fully differential operational preamplifier (FDOA) 92 feeding a differential correlated-double-sampling (CDS) amplifier arrangement 94. CDS switched-capacitor amplifiers 94 obtain low 1/f noise by sampling the signal twice and subtracting the amplifier noise before amplification.

The thermal noise floor of a CDS amplifier 94 is often limited by the size of the input sampling capacitors; large capacitors yield low noise but require huge area and reduce the input impedance of the amplifier. Because the implantable pressure sensing system intermittently acquires samples, large input capacitance is undesirable because it would require longer settling times for the pressure transducer. This would increase the time per sample, which would require more power. In the illustrated amplifier assembly, the chopped preamplifier 92 provides a small amount of gain to the input of the CDS amplifier 94 to allow for the use of capacitors of a practical size and capacity for a low power, in vivo device, while maintaining a high quality signal. The chopping at the input of the preamplifier 92 effectively cancels the 1/f noise that it might otherwise add to the signal.

Returning the FIG. 2, the amplified signal is provided to an analog-to-digital converter (ADC) 66 that digitizes the amplifier signal. In the illustrated implementation, the ADC 66 is implemented as a successive approximation register (SAR) ADC. The digitized signal is then provided to a packet generation component 68. The packet generation component 68 arranges the digitized pressure measurements into an appropriate transmission format and provides them to the transmitter 70 for transmission to an associated base unit (not shown).

In accordance with an aspect of the present invention, the sensor assembly 50 includes an offset removal component 72 employing a low-power, area-efficient method for removing slow pressure changes which might be caused by postural changes by the patient, device orientation shifts, or atmospheric pressure changes. Specifically, the offset removal component 72 calculates a correction factor, as function of an average of a predetermined number of previous samples, to be applied to future measurements. The offset removal component 72 can operate in two modes, automatic and forced. In the automatic mode, the offset removal component 72 seeks to maximize a sensing dynamic range by maintaining the average pressure readings in the center of the instrumentation circuitry. A forced offset calibration is initiated by wirelessly sending a command to the device over the RF recharge link. Once the command is received, the system 50 runs around three hundred times faster than normal to very quickly calculate the average pressure offset and subtract it from the pressure transducer, essentially nulling the system. The forced calibration does not maximize dynamic range, but allows a user or clinician to set the zero level to any reference pressure. Forced calibration automatically ends when the pressure output is less than eight ADC codes, and the system slows down by a factor of three hundred to conserve power.

Whether in automatic or forced mode, the offset removal component 72 operates in substantially the same manner. In one implementation, the offset removal component 72 can include an accumulator to maintain a running average of a predetermined number of previous samples. In one implementation, a twenty-one bit accumulator is used to maintain an average of the last eight thousand samples. A correction value can be calculated as a difference between the full scale range and the average in the automatic mode or a difference between one-half of the full scale range and the average in the forced mode. The correction value represents a pressure offset that is subtracted from the pressure transducer 62 by a bipolar, current-output DAC. The offset cancellation component 72 can also include one or more coarse offset removal current sources. In one implementation, the current-output DAC can be an eight-bit DAC, such that the full scale range is two hundred fifty-five and one-half the full scale range is one hundred twenty-eight.

A power control unit 76 dynamically controls the provision of power to the circuitry 62, 64, 66, 68, 70, and 72. In the illustrated implementation, the implanted battery 52 has a capacity of about three milliamp-hours (mAh), so power management is important in chronic implantations. A six-hour recharge session can replenish 0.6 mAh of capacity, and the sensor system 50 is intended to run for at least forty-eight hours between charges. Accordingly, the time-averaged current consumption for the sensor system 50 must be less than around twelve micro amps.

Achieving such a small current draw for a continuously running implantable telemetry system is not feasible, but the power-control unit 76 leverages the speed ratio between bladder pressure changes and the instrumentation capability. In the illustrated system, for example, bladder pressure is sampled at a rate of between twenty and one hundred hertz, even though instrumentation and telemetry circuits can provide significantly higher sample rates. The power control unit 76 is thus implemented as a suite of very low power circuits that are always running in the background. During normal operation, the device is active for ten millisecond intervals each second. When the device is not active, only the power control unit 76 is consuming power. When the device is active, the power control unit 76 selectively provides power to the vital instrumentation and telemetry circuits such that a sample can be provided with the minimum possible power expenditure. Specifically, each of the components needed to generate and transmit a pressure reading 62, 64, 66, 68, 70, and 72 are provided with power only when their particular function is necessary, such that a given component can be inactive during an active interval of the sensor assembly 50. Without the power control unit 76, the implant consumes over one milliamp from the battery, but when the power control unit is utilized, the time-averaged current is less than nine microamps and the power consumption of the transducer and instrumentation and telemetry circuits is greatly reduced.

Figure 4:
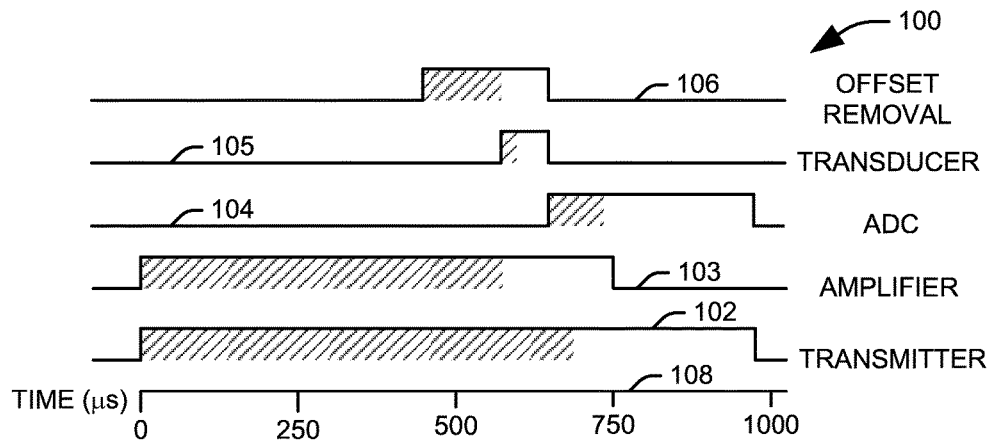
FIG. 4 is a chart illustrating power control signals for various components of an implanted device as a function of time over a one millisecond active interval.

FIG. 4 is a chart 100 illustrating power control signals 102-106 for various components of an implanted device as a function of time, represented on a horizontal axis 108, over a one millisecond active interval. Each power control signal 102-106 is illustrated in FIG. 2 as either "off," represented by a baseline level at which each signal begins, and "on", represented as a signal raised above the baseline. The power control signals 102-106 are complex because they successively turn on circuits as the sampled voltage moves through the instrumentation and telemetry chain. This technique accounts for "warm-up" periods required by certain circuits before they can accurately function, represented by a shaded region in FIG. 4.

It will be noted that the power control signal for the transmitter 102 and the amplifier 103 are on for most of the active cycle, although it will be appreciated that, for many applications, there may be as few as ten such millisecond cycles each second, such that the system is on a minimal stand-by power much of the time. The power control signals for the ADC 104, pressure transducer 105, and offset removal component 106, however, are powered during only a small portion of the active interval, specifically that portion of the active cycle in which they are acquiring or processing the signal. Accordingly, a significant power savings can be realized.

Figure 5:
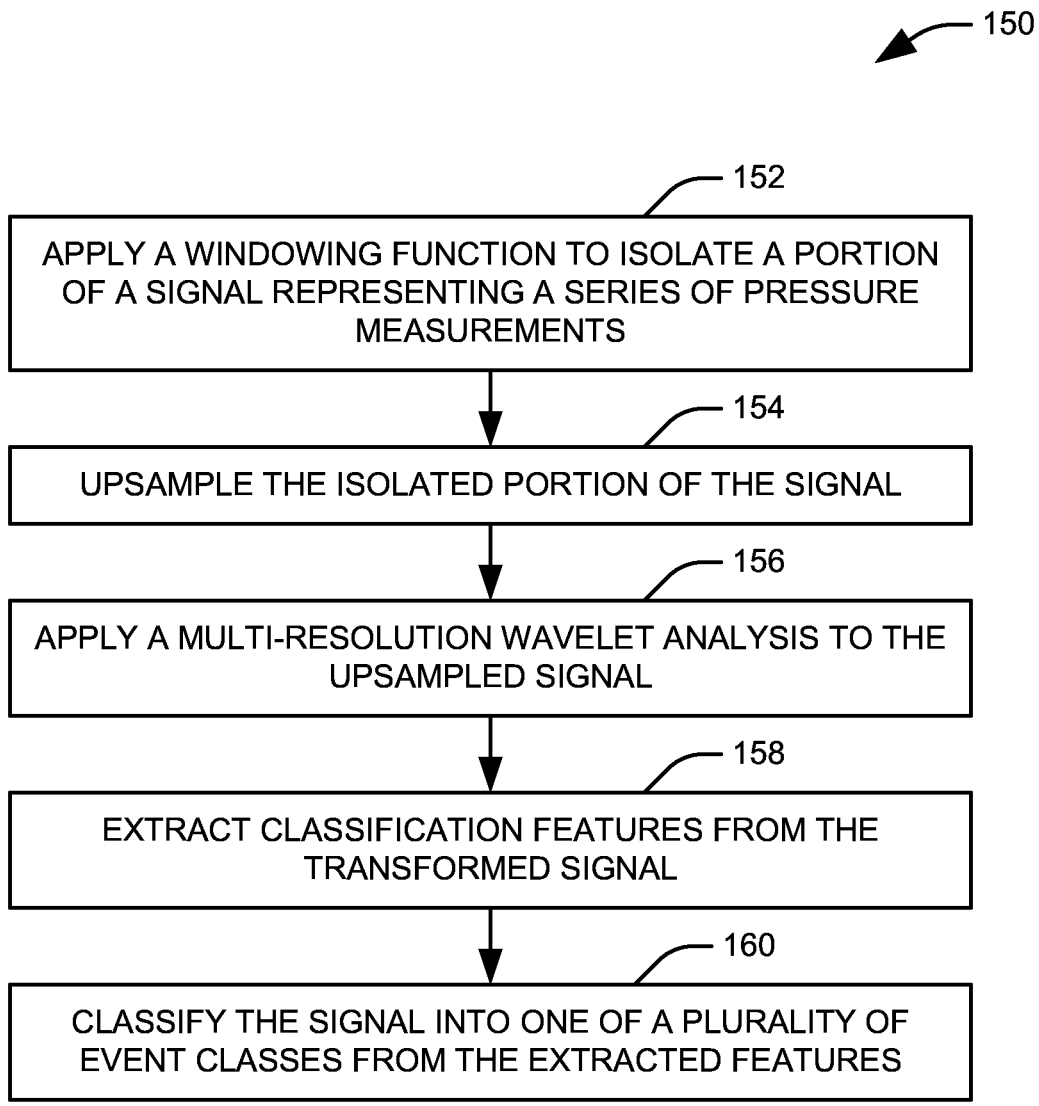
FIG. 5 illustrates a signal-processing method for use in monitoring an output of an in vivo pressure sensor for one or more predetermined events in accordance with an aspect of the present invention.

For neuromodulation applications, an implantable device in accordance with an aspect of the present invention can transmit pressure to an external neural stimulator, with hardware associated with the stimulator monitoring the pressure signals and determining if they are abnormal and require stimulation. FIG. 5 illustrates a signal-processing method 150 for use in monitoring an output of an in vivo pressure sensor for one or more predetermined events in accordance with an aspect of the present invention. It will be appreciated that each of the steps of this method can occur at the event detector 24 of FIG. 1. The method of FIG. 5 is specifically designed to recognize pressure readings representing bladder leaks or unwanted urge spasms for the bladder, but the same concepts could be adapted for control of other organs or for responses other than neural stimulation, such as drug release or similar applications. The signal processing algorithm for pressure monitoring is capable of online real-time identification of bladder and motion events in the presence of noise, amenable to efficient implementation in a microcontroller or digital signal processor, and adaptive to accommodate for variations in event signature, both from subject to subject as well as with time in the same subject. In one implementation, the method of FIG. 5 is implemented using a low-power, sixteen-bit microcontroller in a stimulator.

At 152, windowing is applied to isolate a portion of a signal representing series of pressure measurements. For example, the window can include a predetermined time interval of the signal ending with a most recent measurement. Alternatively, some form of preprocessing, such as a thresholding process, can be used to identify portions of the signal likely to represent events, and an appropriate window can be defined around the identified potential event. At 154, the isolated signal can be upsampled to a desired upsampling frequency.

At 156, a multi-resolution wavelet analysis to is applied to the signal to de-noise the recorded signal. The applied wavelet analysis has been found to efficiently remove background electrical and biological noise and facilitate localization of specific bladder activities. Unlike a Fourier transform, which uses a fixed basis function, wavelet decomposition uses a custom basis function satisfying a set of mathematical constraints that can efficiently identify events in a signal. Time-frequency analysis using a wavelet transform helps distinguish bladder activities from motion events even in situations in which the inventors have found time- and frequency-domain methods fail to distinguish between events. Wavelet transforms are also amenable to on-chip implementation since they can be realized as a bank of high-pass and low-pass filters.

At 158, hyperclusters are identified in the wavelet transform domain and extracted as classification features. For example, the hyperclusters can be identified via a thresholding process applied to the transformed data. At 160, the extracted features are used to classify the signal into one of a plurality of event classes. For example, the events can include bladder voiding, stress, motion, bladder leaks, unwanted urge spasms, and other events of interest.

From the above description of the invention, those skilled in the art will perceive improvements, changes, and modifications. Such improvements, changes, and modifications within the skill of the art are intended to be covered by the appended claims.

Having described the invention, the following is claimed:

1. An in vivo sensor assembly comprising:
a pressure sensor configured to provide an analog signal representing pressure;
a signal conditioning component configured to convert the pressure sensor output into a digital signal;
a transmitter configured to transmit the digital signal to an external base unit; and
a power control unit configured to transition the in vivo sensor assembly from an inactive mode to an active mode having an active measurement interval at a predetermined frequency and to dynamically allocate power throughout the implantable sensor assembly, each of the pressure sensor, the signal conditioning component, and the transmitter having a necessary power interval during the active measurement interval with the power allocated by the power control unit such that during the active measurement interval, each of the pressure sensor, the signal conditioning component, and the transmitter are powered only for the associated necessary power interval to perform a related function, the necessary power interval being less than all of the active measurement interval, such that each of the signal conditioning component, and the transmitter are not powered for at least part of the active measurement interval.

2. The in vivo sensor assembly of claim 1, wherein the active measurement interval has a duration of approximately one millisecond, and the predetermined frequency is between twenty and one hundred hertz.

3. The in vivo sensor assembly of claim 1, wherein the signal conditioning component comprises an offset removal component configured to calculate a correction value for the output of the pressure sensor as a function of an average of a predetermined number of previous samples.

4. The in vivo sensor assembly of claim 3, wherein the offset removal component calculates the correction value as a difference between the a full-scale range of a digital-to-analog converter associated with the transmitter and an average of a predetermined number of previous samples to maximize a sensing dynamic range of the in vivo sensor assembly.

5. The in vivo sensor assembly of claim 3, wherein the signal conditioning component comprises an offset removal component responsive to an external command, the offset removal component being configured to, in response to the external command, instruct the sensor to take a plurality of measurements over a short period of time, the signal offset component calculating a correction value as an average of the plurality of measurements as to null the system.

6. The in vivo sensor assembly of claim 1, wherein each of the signal conditioning component, the transmitter, and the power control unit are implemented as a single application-specific integrated circuit chip.

7. The in vivo sensor assembly of claim 1, wherein the transmitter is powered during a portion of the active measurement interval for which neither of the signal conditioning component nor the pressure sensor is powered.

8. The in vivo sensor assembly of claim 7, wherein the signal conditioning component is powered during a portion of the active measurement interval for which the pressure sensor is not powered.

9. An in vivo sensor assembly comprising:
a pressure sensor configured to provide an analog signal representing pressure;
a signal conditioning component configured to convert the pressure sensor output into a digital signal;
a transmitter configured to transmit the digital signal to an external base unit; and
a power control unit configured to transition the in vivo sensor assembly from an inactive mode to an active mode having an active measurement interval at a predetermined frequency and to dynamically allocate power throughout the implantable sensor assembly, each of the pressure sensor, the signal conditioning component, and the transmitter having a necessary power interval during the active measurement interval with the power allocated by the power control unit such that during the active measurement interval, each of the pressure sensor, the signal conditioning component, and the transmitter are powered only for the associated necessary power interval necessary to perform a related function, the necessary power interval being less than all of the active measurement interval, such that each of the signal conditioning component, the pressure sensor, and the transmitter are not powered for at least part of the active measurement interval.

* * * * *